US010046110B2

(12) United States Patent
Poulsen et al.

(10) Patent No.: US 10,046,110 B2
(45) Date of Patent: Aug. 14, 2018

(54) LOCK FOR DRUG INJECTION DEVICE

(71) Applicant: BAYER PHARMA AKTIENGESELLSCHAFT, Berlin (DE)

(72) Inventors: Sven Erik Poulsen, Skive (DK); Jan Olesen, Holstebro (DK); Carsten Pedersen, Holstebro (DK)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 469 days.

(21) Appl. No.: 14/761,584

(22) PCT Filed: Jan. 13, 2014

(86) PCT No.: PCT/EP2014/050452
§ 371 (c)(1),
(2) Date: Jul. 16, 2015

(87) PCT Pub. No.: WO2014/111332
PCT Pub. Date: Jul. 24, 2014

(65) Prior Publication Data
US 2015/0335822 A1    Nov. 26, 2015

(30) Foreign Application Priority Data

Jan. 16, 2013   (EP) .................................. 13151386

(51) Int. Cl.
*A61M 5/20*   (2006.01)
*A61M 5/145*  (2006.01)

(52) U.S. Cl.
CPC ............ *A61M 5/1456* (2013.01); *A61M 5/20* (2013.01); *A61M 2005/2073* (2013.01)

(58) Field of Classification Search
CPC .................. A61M 5/1456; A61M 5/20; A61M 2005/2073
(Continued)

(56) References Cited

U.S. PATENT DOCUMENTS

2008/0269689 A1    10/2008   Edwards et al.
2014/0114277 A1*   4/2014    Eggert .................... A61M 5/20
                                                                      604/500

FOREIGN PATENT DOCUMENTS

CA    2786783 A1    7/2011
EP    2253348       11/2010
(Continued)

OTHER PUBLICATIONS

International Search Report dated Jun. 4, 2014 for PCT Application No. PCT/EP2014/050452 filed Jan. 13, 2014, 3 pages.
(Continued)

*Primary Examiner* — Phillip Gray
(74) *Attorney, Agent, or Firm* — Morrison & Foerster LLP

(57) ABSTRACT

A drug injection device comprises a main body case, a drug syringe mounting component, a piston, a drive mechanism, a controller, and means for locking the lid during operation of the drug injection device. The main body case has a lid and a base and an injection needle let-in/let-out opening. The drug syringe mounting component is provided inside the main body case, and allows a (filled) drug syringe to be mounted therein. The piston is movable with respect to the drug syringe mounting component. The drive mechanism drives the drug syringe mounting component and the piston. The controller is electrically connected to the drive mechanism. The means for locking the lid during operation of the (Continued)

Figure 1:
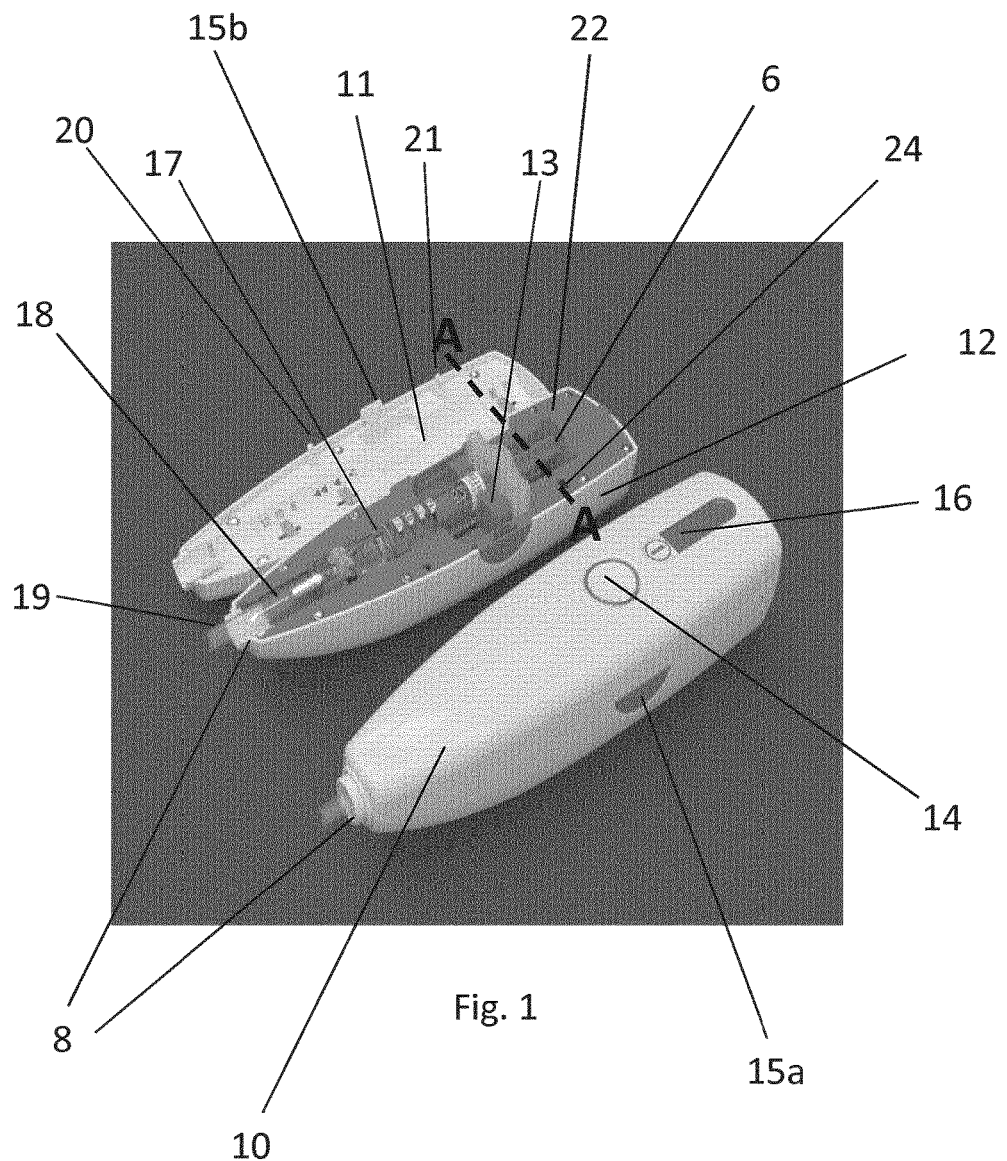

drug injection device is activated and deactivated by movement of the drug syringe mounting component when the lid is closed.

18 Claims, 4 Drawing Sheets

(58) Field of Classification Search
USPC .......................................................... 604/135
See application file for complete search history.

(56) References Cited

FOREIGN PATENT DOCUMENTS

| EP | 2253348 A1 | 11/2010 |
|---|---|---|
| EP | 2384778 | 11/2011 |
| JP | 2008-528210 | 7/2008 |
| JP | 2013-517023 | 5/2013 |
| WO | WO-2006083876 A2 | 8/2006 |
| WO | WO-2009125582 A1 | 10/2009 |
| WO | WO-2011085797 A1 | 7/2011 |
| WO | WO-2012160159 | 11/2012 |
| WO | WO-2012160160 | 11/2012 |

OTHER PUBLICATIONS

Preliminary Report on Patentability dated Jul. 21, 2015 for PCT Application No. PCT/EP2014/050452 filed Jan. 13, 2014, 5 pages.

\* cited by examiner

LOCK FOR DRUG INJECTION DEVICE

CROSS REFERENCE TO RELATED APPLICATIONS

This application is the national stage of International Application No. PCT/EP2014/050452, filed internationally on Jan. 13, 2014, which claims the benefit of European Application No. 13151386.3, filed Jan. 16, 2013.

The present invention relates to a drug injection device.

A conventional drug injection device has a main body case, an injection needle let-in/let-out opening that is an opening for letting an injection needle in and out of the main body case, a drug syringe mounting component that is provided inside the main body case and in which a (filled) drug syringe is mounted, a piston that is able to move with respect to this drug syringe mounting component, a drive mechanism that drives the piston, and a control circuit that is electrically connected to this drive mechanism. With this drug injection device, when the piston is moved so that sealing rubber within the drug syringe is pushed, the drug is automatically injected into the patient's body through an injection needle mounted at the distal end of the drug syringe (see, for example, EP 2384 778 A1).

However, the drug injection device is sometimes not handled properly by the user. For example, if the user mounting a (filled) drug syringe within the main body case, closing the lid of the main body case and starting the injection procedure and then opens the main body. In that situation the user might get injured, if he touches moving parts inside the main body case, or he might damage the (moving) drug syringe or the mechanics for movement of the drug syringe mounting component or of the piston or he might just interrupt the injection.

In view of this, it is an object of the present invention to provide a drug injection device which comprises safety measures to prevent the user from opening the lid of the main body case after the injection procedure has been started and before it is terminated.

The drug injection device pertaining to the present invention comprises a main body case, a drug syringe mounting component, a piston, a drive mechanism, a controller, and means for locking the lid during operation of the drug injection device. The main body case has a lid and a base and an injection needle let-in/let-out opening. The drug syringe mounting component is provided inside the main body case, and allows a (filled) drug syringe to be mounted therein. The piston is movable with respect to the drug syringe mounting component. The drive mechanism drives the drug syringe mounting component and the piston. The controller is electrically connected to the drive mechanism. The means for locking the lid during operation of the drug injection device is activated and deactivated by movement of the drug syringe mounting component when the lid is closed.

Preferably the drug injection device comprises further a sensor adapted to signal the controller when the lid is closed to allow the controller to drive the drug syringe mounting component and the piston.

Preferably the drug syringe mounting component is movable forth and back between a position where the injection needle of the drug syringe is inside the main body case, the mounting position, and a position where the injection needle extends through the injection needle let-in/let-out opening, the injection position. In case the injection needle let-in/let-out opening of the drug injection device is brought near the skin of a patient and the injection is initiated by the patient, the movement of the drug syringe mounting component with a drug syringe being mounted to it towards the injection position causes the skin of the patient to be automatically pierced by the injection needle. While the drug syringe mounting component is in the injection position, the piston is be moved automatically by the drive mechanism to eject the drug from the syringe barrel through the syringe needle into the body of the patient. After termination of the injection the drug syringe mounting component is moved backwards from the injection position to the mounting position.

In a preferred embodiment the drug syringe mounting component is a sledge to which the drug syringe can be removably attached.

In one embodiment the drive mechanism comprises a drive means for the piston and another separate drive means for the drug syringe mounting component. Preferably the drive means for the piston is attached to the drug syringe mounting component. The drive means for piston and drug syringe mounting component can be electromechanical motors or spring driven systems.

In one embodiment the drug syringe mounting component is mounted within the base. The means for locking the lid comprise a first locking means connected to the lid and adapted to interact with a second locking means connected to the drug syringe mounting component such that the lid and the drug syringe mounting component cannot be separated from one another during interaction. Interaction occurs only when the lid is closed upon movement of the drug syringe mounting component away from the mounting position. When the drug syringe mounting component arrives back from another position, i.e. the injection position to the mounting position then the interaction between the locking means of the lid and the drug syringe mounting component terminates.

The first locking means can be at least one hook extending from the to the inside of the main body case lid towards the drug syringe mounting component and the second locking means can be a longitudinal (in moving direction of the drug syringe mounting component) rim extending laterally from at least one side of the drug syringe mounting component. The at least one rim is adapted to be caught by the at least one hook when the lid is closed and the drug syringe mounting component is moved away from the mounting position. Alternatively the hook and the rim can be replaced by a loop extending from the lid and a rod attached laterally to the drug syringe mounting component or other similar pairs of structures adapted to engage with one another.

In another preferred embodiment the lid is hingedly connected to the base and the first and second locking means are located at the side of the lid and the drug syringe mounting component which is opposite to the hinge.

In an alternative embodiment the lid can be fully removed from the base. In that case the lid has two first locking means arranged facing to the inside of the main body case at opposite sides of the lid and the drug syringe mounting component has two corresponding second locking means.

The drug injection device may comprise at least one opening means adapted to reversely lock the lid to the base. Such opening means can be at least one opening button arranged at the base or the lid. The opening button locks the main body case by means of corresponding mechanically engaging parts between lid and base which can be disengaged by actuating (pressing, turning or the like) the opening button. The opening button is located at the lid and base on the side of the main body case opposite to the hinge between lid and base or, if the lid can be fully separated from the base, there are at least two opening buttons on two opposite sides of the main body case. The one or more opening buttons do not work when the lid is closed and the means for locking the lid during operation of the drug injection device is activated as described above.

In an alternative embodiment the drug injection device comprises at least one opening means adapted to reversely lock the lid to the base. The opening means lock the main body case by means of corresponding mechanically engaging parts between lid and base which can be disengaged by actuating the opening means. In this alternative embodiment the means for locking the lid prevent the opening means from being actuated by blocking it mechanically.

Such blocking occurs only when the lid is closed upon movement of the drug syringe mounting component away from the mounting position. When the drug syringe mounting component arrives back from another position, i.e. the injection position to the mounting position then the blocking of the opening button terminates.

Such opening means can be at least one opening button arranged at the base or the lid. Such opening button can be actuated by pressing, turning or the like.

Preferably the opening button is located at the lid and base on the side of the main body case opposite to the hinge between lid and base or, if the lid can be fully separated from the base, there are at least two opening buttons on two opposite sides of the main body case. In case of two opening buttons the means for locking the lid prevents both opening buttons from being actuated by blocking them mechanically.

In one embodiment the opening button can be actuated by pressing a portion of the opening button located at the lid or base which then disengages from a corresponding portion of the opening button at the base or lid by movement towards the interior of the main body case. The movement of the opening button can be blocked by a rod connected to the drug syringe mounting component when it is moved away from the mounting position.

In another embodiment the rod is not connected to the drug syringe mounting component but the rod is advanced by an electromagnetic actuator. The electromagnetic actuator is triggered by the control or by a switch/sensor which emits a signal when the drug syringe mounting component is moved away from the mounting position.

With the drug injection device of the present invention, opening of the lid of the main body case is prevented during the injection procedure. This safeguards the user from being injured by touching any moving parts inside the main body case and safeguards the drug injection device and drug syringe from being damaged during operation and allows an uninterrupted injection.

FIGURES AND EXAMPLES

FIG. 1 Drug injection device with open and with closed lid

Figure 2:
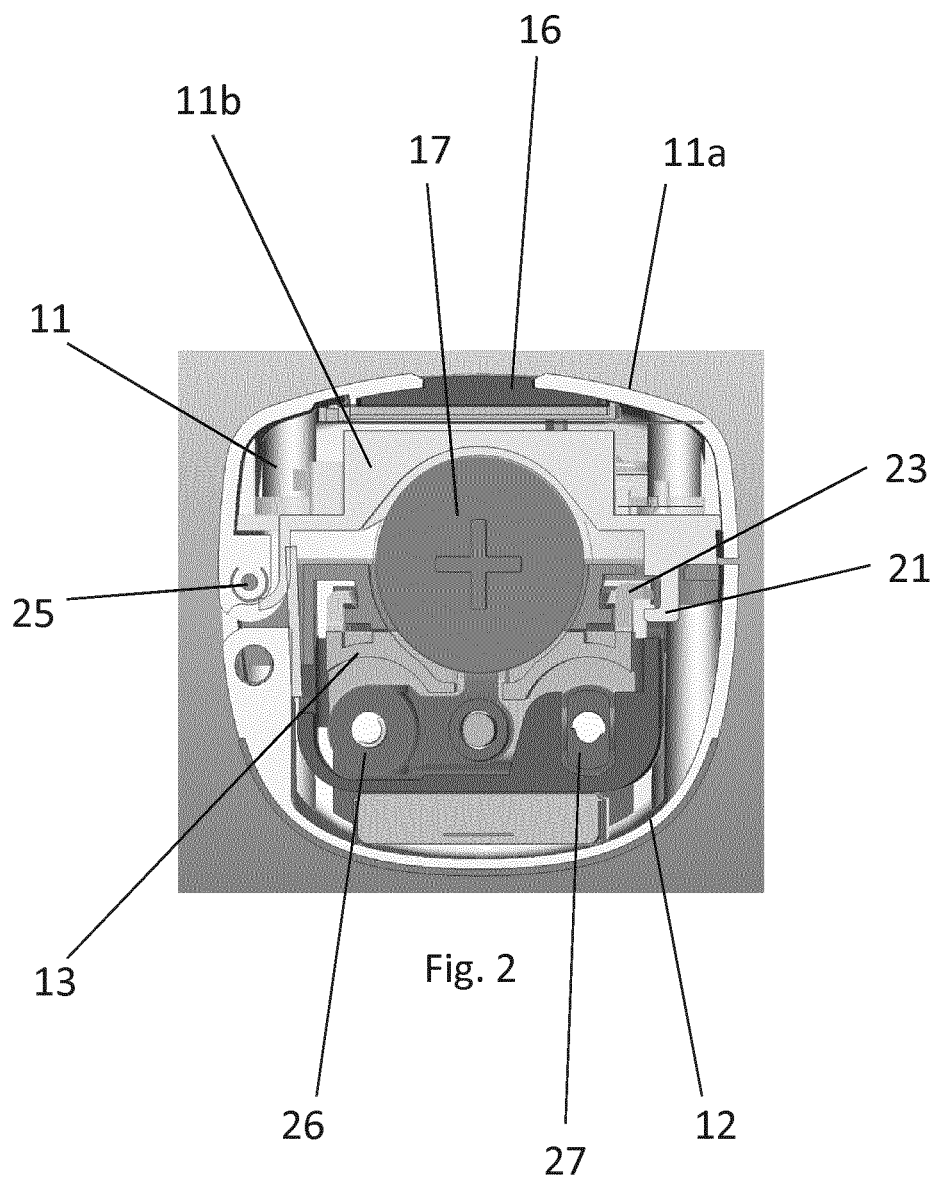

FIG. 2 Cross-sectional view of drug injection device along line A-A with syringe mounted FIG. 3a-e Cross-sectional views of drug injection device along line A-A without syringe mounted FIG. 1 shows on the left side the drug injection device with open lid and on the right side the drug injection device with the lid closed.

The drug injection device has a main body case 10. The main body case 10 has a lid 11 and a base 12 and an injection needle let-in/let-out opening 8. The lid 11 is hingedly connected to the base 12 by means of hinge 25 (see FIG. 2). A guide pin 20 aligns the lid 11 with the base 12 when closing the lid 11. An actuation button 14 for starting an automatic injection procedure including piercing by a drug syringe needle and ejecting the contents of the drug syringe is provided at the outside of the main body case 10 as well as a display 16 for signaling information about the status of the injection device or the injection procedure. An opening button 15a provided at the base 12 has to be pressed to open the lid 11 when it is closed. Upon pressing the opening button 15a a locking piece 15b attached to the lid 11 disengages from the opening button 15 such that the lid 11 can be opened.

A sledge 13 is provided inside the main body case 10 and allows a drug syringe 17 to be mounted thereon. The drug syringe 17 has a syringe barrel filled with a drug. The syringe barrel has an open end and a needle end. In the syringe barrel there is a movable sealing rubber which closes the open end of the syringe barrel. A piston rod 6 in contact with the movable sealing rubber can be moved towards the needle end of the drug syringe 17 by the piston 29 which is driven by the electromechanical motor 26 (see FIG. 3b). A needle 18 is attached to the needle end of the drug syringe barrel and has a needle cover 19. The needle cover 19 has to be removed prior to starting the injection procedure. The piston 29 which is in contact with the piston rod 6 of the syringe 17 is movable with respect to the sledge 13. Electromechanical motors 26, 27 (see FIG. 2) drive the sledge 13 and the piston 29.

The controller is electrically connected to the electromechanical motors 26, 27. The cover 22 is provided inside the base 12 to hide the electromechanical motors 26, 27 and all other components which need not to be accessed by the user.

FIG. 2 is a cross-sectional view of the drug injection device shown in FIG. 1 taken along line A-A. The lid 11 comprises a shell 11a and a top plate 11b. The top plate 11b has a hook 21 (which can also be seen in FIG. 1) extending from the lid 11 towards the sledge 13 and which interacts with a rim 23 extending laterally from that side of the sledge 13 which is opposite to the hinge 25. The lid 11 is closed and the rim is catched by the at least one hook such that the lid 11 cannot be opened.

Figure 3A:
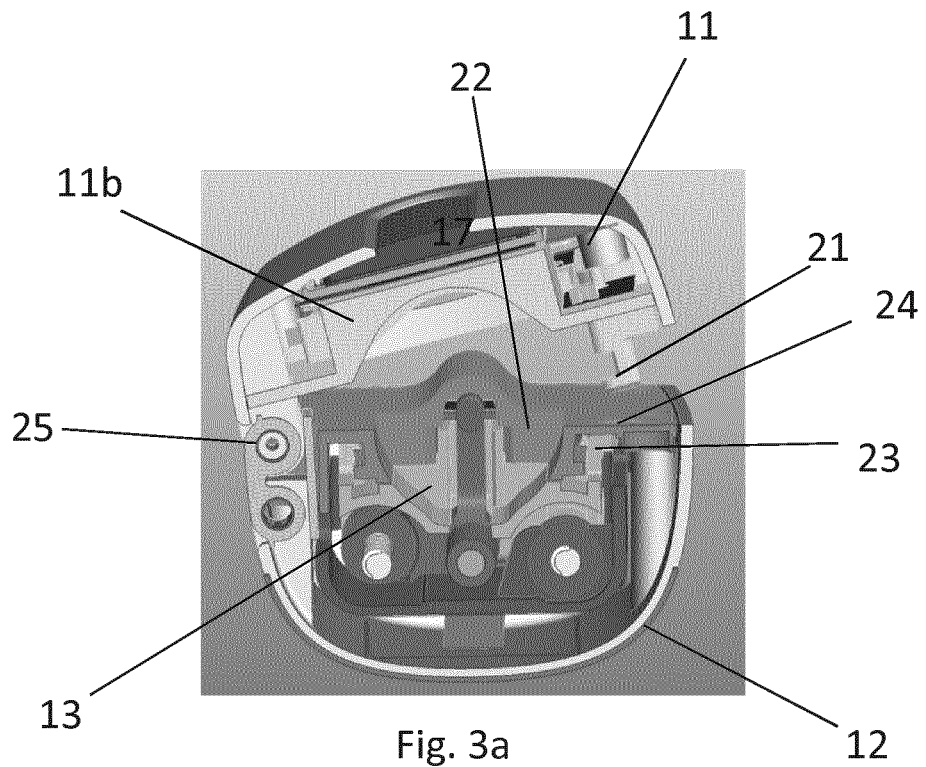
Figure 3B:
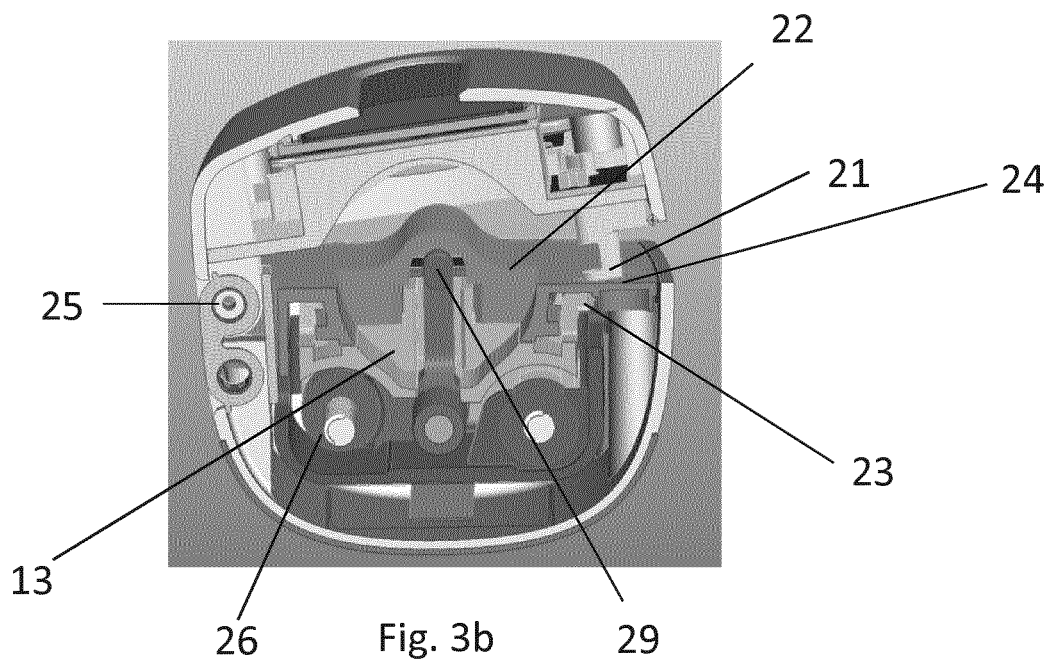
Figure 3C:
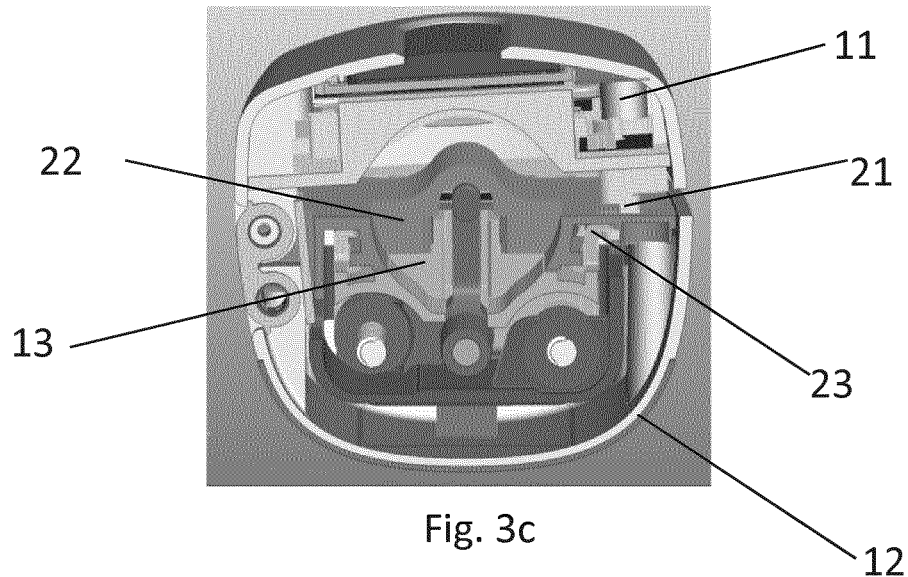
Figure 3D:
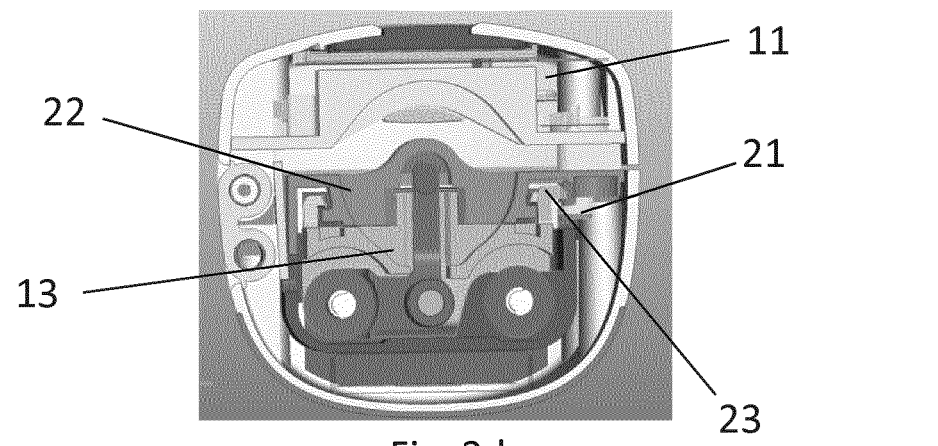
Figure 3E:
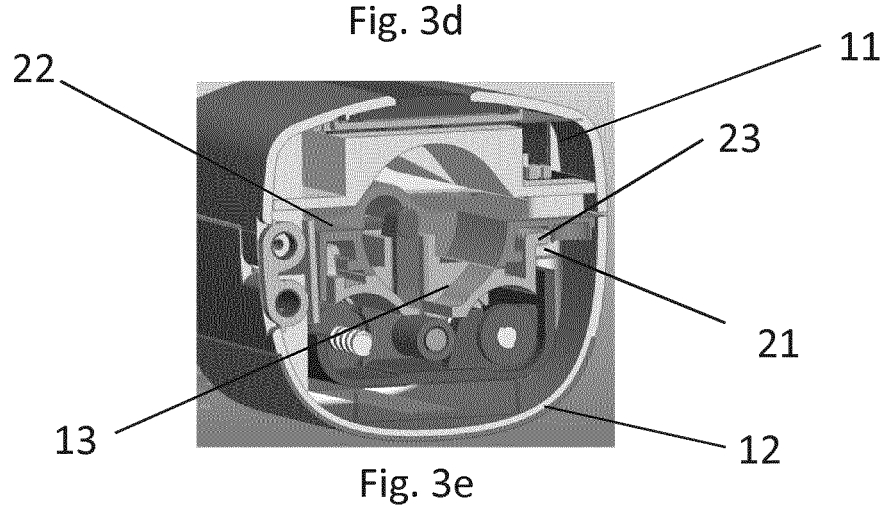

FIGS. 3a to 3e show in a series of cross-sectional views of the drug injection device taken along line A-A but without syringe mounted how the lid 11 is being locked during operation of the drug injection device. In FIGS. 3a to 3c the lid 11 is moved from an open position to a closed position. The sledge 13 is in the mounting position in which a drug syringe 17 can be mounted on it when the lid (11) is open. Upon closure of the lid (11) the hook 21 moves downward towards the base (12) and the cover 22. The cover 22 has an aperture 24 through which hook 21 sticks out when the lid 11 is in the closed position (FIG. 3c) such that the hook 21 is in the lock position. The rim 23 of the sledge 13 does not interact with the hook 21 when the sledge 13 is in the mounting position. In FIG. 3d the sledge 13 has been moved away from the mounting position and the rim 23 is catched by the hook 21. Now the lid 11 is locked (to the sledge 13) and cannot be opened unless the sledge 23 moves back to the mounting position. Also pressing the opening button 15a which would release the engagement between the top shell 11a of the lid with the base 12 would not allow to open the lid 11. FIG. 3e shows the same situation as FIG. 3d but in a perspective view. In FIG. 3e it can be recognized that the rim 23 extends over a certain distance in moving direction of the sledge 13 such that rim 23 is able to catch the hook 21 in all possible positions of the sledge 13 other than the mounting position.

The invention claimed is:

1. A drug injection device, comprising:
    a main body case having a lid, a base, and an injection needle let-in/let-out opening;
    a drug syringe mounting component provided inside the main body case for mounting a drug syringe therein, the drug syringe mounting component being movable forward and backward between a position where an injection needle of the drug syringe is inside the main body case and a position where the injection needle extends through the injection needle let-in/let-out opening;
    a piston that is movable with respect to the drug syringe mounting component;
    a drive mechanism for driving the drug syringe mounting component forward and backward;
    a controller electrically connected to the drive mechanism; and
    a lock for locking the lid when the lid is closed by movement of the drug syringe mounting component from the position where the injection needle of the drug syringe is inside the main body case to the position where the injection needle extends through the injection needle let-in/let-out opening.

2. The drug injection device of claim 1, further comprising a sensor adapted to signal the controller when the lid is closed to allow the controller to drive the drug syringe mounting component and the piston.

3. The drug injection device of claim 1, wherein the drug syringe mounting component is a sledge to which the drug syringe can be removably attached.

4. A drug injection device of claim 1, wherein the drive mechanism comprises a drive for the piston and another drive for the drug syringe mounting component.

5. A drug injection device of claim 4, wherein the drive for the piston is attached to the drug syringe mounting component.

6. A drug injection device of claim 4, wherein the drive for the piston and the drive for the drug syringe mounting component are electromechanical motors or spring driven systems.

7. A drug injection device of claim 1, wherein the drug syringe mounting component is mounted within the base.

8. A drug injection device of claim 1, wherein the lock for locking the lid comprises a first locking means connected to the lid and adapted to interact with a second locking means connected to the drug syringe mounting component such that the lid and the drug syringe mounting component cannot be separated from one another during interaction, wherein interaction occurs only when the lid is closed and the drug syringe mounting component is moved away from a mounting position.

9. A drug injection device of claim 8, wherein the first locking means comprises at least one hook extending from the lid towards the drug syringe mounting component and the second locking means comprises a longitudinal rim extending laterally from a least one side of the drug syringe mounting component, and wherein the longitudinal rim is adapted to be catched by the at least one hook when the lid is closed and the drug syringe mounting component is moved away from the mounting position.

10. A drug injection device of claim 8, wherein the lid is hingedly connected to the base and the first and second locking means are located at the side of the lid and the drug syringe mounting component is opposite to the hinge.

11. A drug injection device of claim 8, wherein the lid has two first locking means arranged facing the inside of the main body case at opposite sides of the lid and the drug syringe mounting component has two corresponding second locking means.

12. A drug injection device of claim 1, further comprising at least one opening means for the main body case which is adapted to reversely lock the lid to the base.

13. A drug injection device of claim 1, further comprising at least one opening means for the main body case which is adapted to reversely lock the lid to the base by corresponding mechanically engaging parts between the lid and the base, wherein the lock for locking the lid is adapted to prevent the at least one opening means to be actuated to open the closed lid by blocking the at least one opening means mechanically when the drug syringe mounting component is positioned away from the mounting position.

14. A drug injection device of claim 13, wherein the opening means comprises at least one opening button arranged at the base or the lid, and the opening button can be actuated by pressing or turning.

15. A drug injection device of claim 14, wherein the opening means is located at the lid and base on the side of the main body case opposite to the hinge between the lid and base.

16. A drug injection device of claim 14, wherein the lid can be fully separated from the base, at least two opening means are provided on two opposite sides of the main body case, and the lock for locking the lid prevents both opening means from being actuated by blocking both opening means mechanically.

17. A drug injection device of claim 14, wherein the opening means is actuated by pressing the opening button located at the lid or base which then disengages a locking piece at the base or lid by movement towards the interior of the main body case, and wherein the movement of the opening button is blocked by a rod connected to the drug syringe mounting component when the drug syringe mounting component is moved away from the mounting position.

18. A drug injection device of claim 14, wherein the opening means is actuated by pressing a portion of the opening button located at the lid or base which then disengages a locking piece at the base or lid by movement towards the interior of the main body case, wherein the movement of the opening button is blocked by a rod, and wherein the rod is advanced by an electromagnetic actuator and the electromagnetic actuator is triggered by the control or by a switch/sensor which emits a signal when the drug syringe mounting component is moved away from the mounting position.

* * * * *